United States Patent [19]

Harper et al.

[11] 4,032,563
[45] June 28, 1977

[54] PROCESS FOR THE RECOVERY OF HIGH PURITY DIESTERS OF TEREPHTHALIC OR ISOPHTHALIC ACIDS

[75] Inventors: Jon J. Harper, Naperville; Antonio E. Navarrete, Downers Grove, both of Ill.; Richard J. Thomas, Huntington Beach, Calif.

[73] Assignee: Standard Oil Company, Chicago, Ill.

[22] Filed: Sept. 2, 1975

[21] Appl. No.: 609,193

[52] U.S. Cl. .......................... 260/475 R; 260/475 B
[51] Int. Cl.² ................... C07C 69/80; C07C 69/82
[58] Field of Search ............ 260/475 B, 475 R, 475

[56] References Cited

FOREIGN PATENTS OR APPLICATIONS

| 65-15061 | 7/1965 | Japan | 260/475 B |
| 978,172 | 12/1964 | United Kingdom | 260/475 B |

*Primary Examiner*—Jane S. Myers
*Attorney, Agent, or Firm*—Robert E. Sloat; Arthur G. Gilkes; William T. McClain

[57] ABSTRACT

A process is disclosed for producing the dimethyl esters of aromatic dicarboxylic acids wherein the acid is esterified with a low molecular weight alcohol, the product is crystallized and separated to isolate a mass of the diester crystals and recover a mother liquor. An improvement in such process resides in the thermal oxidation with molecular oxygen of a mother liquor material to produce a mono methylphthalate from either p-methyl toluate or methyl-4-carboxybenzaldehyde. A portion of the oxidized mother liquor is recycled to the esterification zone wherein the mono methylphthalate can be esterified to the dimethyl ester while another portion of the oxidized mother liquor stream is passed to an evaporation treatment zone, preferably a wiped film evaporator, wherein overhead material is separated from a high boiling bottoms material and recycled to the esterification reaction zone. The high boiling bottoms stream from the evaporation treatment zone is purged from the system thereby removing from the overall process high boiling organics including ash.

23 Claims, 1 Drawing Figure

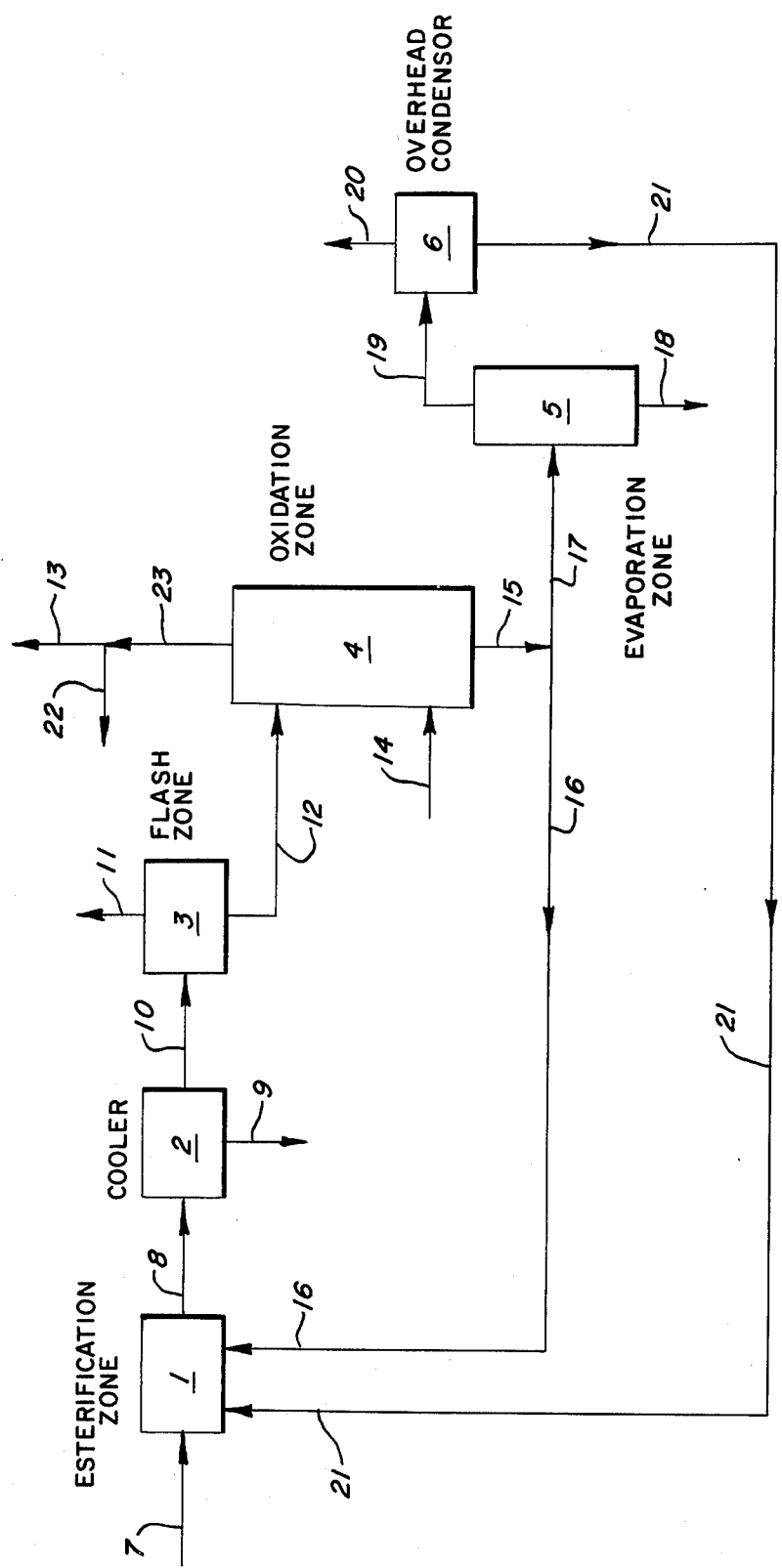

PROCESS FOR THE RECOVERY OF HIGH PURITY DIESTERS OF TEREPHTHALIC OR ISOPHTHALIC ACIDS

BACKGROUND OF THE INVENTION

1. Field of the Invention

The field of art to which this invention pertains is purification of diesters of phenylene dicarboxylic acids, in particular, the purification of the diesters of terephthalic or isophthalic acids, by an oxidation treatment of mother liquor in conjunction with evaporation treatment of the oxidized mother liquor, thereafter a bottoms stream of high boiling organics and ash is recovered, and a low boiling overhead material is returned to the esterification zone.

2. Description of the Prior Art

Relevant prior art includes Japanese Patent Publication No. 15016/65 (Application No. 55066/62). Disclosed in this publication is an improvement in a process for producing terephthalic or isophthalic, acid diesters in which material such as (1) a residual liquid obtained by further distillation or concentration of a mother liquor which has been separated from the crystallized diester and/or (2) the low boiling distillate which is obtained from the distillation of the crystallized diester, is oxidized and then returned for recirculation into an esterification zone. The primary impurities described in either the concentrated mother liquor or the low boiling material removed from the diester crystals is thought, according to the Japanese Publication, to be a formylbenzoic acid methyl ester which upon oxidation forms a mono methyl ester of terephthalic or isophthalic acid.

In the subject Japanese Publication, a portion of the mother liquor is subjected to a treatment for decolorization by means of distillation or the like and then delivered directly to the esterification zone as recycle without oxidation treatment. The portion of the mother liquor into which terephthalic or isophthalic acid diester has migrated or has been concentrated contains a significant amount of impurities (formylbenzoic acid methyl ester) and is delivered to an oxidation reactor and then returned to the esterification reaction zone.

SUMMARY OF THE INVENTION

The present invention comprises an improvement in a process for the production of lower alkyl esters of phenylene dicarboxylic acids in an esterification zone wherein the effluent from such zone is cooled thereby forming crystals of diester product and a mother liquor stream, the latter being recycled to the esterification zone. The improvement in the process generally comprises an oxidation treatment of the mother liquor to convert impurities present in such mother liquor-namely, including in most instances but not limited to p-methyl toluate, methyl-4-carboxybenzaldehyde and bis (carbomethoxy) benzylbenzoate-- to their respective acid esters with return of a portion of the oxidized mother liquor to the esterification zone, and the evaporation treatment of a remaining portion of said oxidized mother liquor to effect the production of a low boiling overhead stream which is returned to the esterification reaction zone and a high boiling bottoms product which contains high boiling organics, ash and, in some instances, catalyst which is removed from the processing system by purge.

In a broad embodiment, the present invention resides in a process for the production of lower alkyl esters of a phenylene dicarboxylic acid in an esterification zone wherein reaction product from said zone is cooled, thus rendering a mass of lower alkyl ester separable from remaining mother liquor containing impurities characterized as high boiling organics, ash and methyl esters of carboxybenzaldehyde and toluic acid wherein an improvement comprises:

1. oxidation treatment of mother liquor to form a product termed oxidized mother liquor and return of part of said oxidized mother liquor to the esterification zone;
2. evaporation treatment of another part of said oxidized mother liquor to effect production of low boiling overhead and a high boiling bottoms product containing said high boiling organics and ash;
3. return of overhead product to the esterification zone with removal of high boiling bottoms product of the evaporation treatment from the process.

These and other objects and embodiments of the invention will be easily ascertained from a further reading of the specification and attached claims.

BRIEF DESCRIPTION OF THE DRAWING

The attached DRAWING shows, in a brief description, an esterification zone 1 which is connected to a cooler 2, a flash zone 3, an oxidation zone 4, and an evaporation zone 5 associated with an overhead condenser 6. These specific units in the overall process effect the production of a lower alkyl ester of a phenylene dicarboxylic acid from the acid and a lower alkyl alcohol such as methanol.

More particularly, esterification zone 1 has a feed line 7 passing into it wherein the phenylene dicarboxylic acid, typically terephthalic or isophthalic acid, along with catalyst and a lower alkyl alcohol, typically methanol, are passed to be esterified for the production of the diester. In the esterification zone there is a suitable contacting at pressure and temperature conditions to effect the conversion of the acid to the ester. Associated separation, temperature and pressure control means and contacting apparatus are not shown for simplicity of process description. Also shown passing into the esterification zone 1 is an oxidized mother liquor stream 16 which is directly recycled from the oxidation zone 4 and a low boiling overhead product which is derived from evaporation zone 5 which passes to the esterification zone via line 21. The overall description of these streams 16 and 21 will be described in more detail below.

Stream 8 which is removed from the esterification zone 1 typically will contain the lower alkyl esters produced from the phenylene dicarboxylic acid along with unconverted alcohol, the methyl esters of carboxybenzaldehyde and toluic acid, high boiling organics, ash and in some instances entrained catalyst. This stream is passed via line 8 into cooler 2 which can function to remove an essentially purified lower alkyl diester of the acid fed to the esterification zone by crystallization and separation using either filtration or centrifugation methods. The recovered crystalline diester passing through line 9 may be sent to other processing wherein light end materials are removed and either returned to the esterification zone, removed from the process, or in some instances passed to an oxidation zone. Line 10 which leaves the cooler 2 is typically referred to as a mother liquor stream and contains uncrystallized diesters, unreacted lower alcohols, some entrained catalyst from the esterification zone, materials referred to as the methyl esters of carboxybenzaldehyde and toluic acid, namely, methyl-4-carboxybenzaldehyde and p-methyl toluate respectively, and high boiling organics including in some instances bis (carbomethoxy) benzylbenzoate. The latter three materials, if not subjected to further treatment such as oxidation, will eventually either have to be removed from the system or allowed to contribute to excessive recycling greatly reducing the overall efficiency of the process. It is because of these particular materials that the present oxidation of essentially all of the mother liquor in a preferred instance is performed converting these materials to the mono methyl esters of the dicarboxylic acid.

The above-described mother liquor stream is passed via line 10 into a flash zone 3 wherein a portion of material is flashed off. The overhead product removed via line 11 generally comprises water and the lower alkyl alcohol plus light ester by-products which are removed from the process. It is desired to remove these low end or light boiling materials in order to eliminate the possibility of explosions within the processing sequence since these materials when contacted with an oxygen atmosphere can form explosive mixtures.

The light ends being removed, there is left a stream 12 which is removed from the flash zone 3. This stream is typically referred to as a mother liquor stripper bottoms stream and except for the material removed in the flash zone 3, is essentially the same as the mother liquor stream removed via line 10 from the cooler. In a preferred instance, essentially all the mother liquor stripper bottoms stream is passed into the oxidation zone 4. Into the oxidation zone 4 a stream containing molecular oxygen is passed via line 14. Removed from the oxidation zone 4 via line 23 is the unreacted oxygen, by-product water and small portions of lower alkyl alcohol and light ends either produced in the oxidation zone or not totally removed in the flash zone 3 and traces of diester. In instances where enriched air or purified oxygen streams are used, the effluent line 13 may be treated for recycle to the oxidation zone 4. Line 22 carries water, light esters and some dimethyl ester product and generally is recycled to esterification zone 1.

The product removed from oxidation zone 4 via line 15 represents material termed oxidized mother liquor. This material is split, depending upon the upstream operations, into a stream which can be recycled directly to the esterification zone 1 via line 16 and a portion which can be passed to the evaporation zone 5. In a preferred instance, the portion of the oxidized mother liquor stream not recycled directly to the esterification zone is passed via line 17 to the evaporation zone 5.

In the evaporation zone an evaporation treatment takes place to effect the production of a low boiling overhead product which is recovered in overhead condenser 6 and returned to the esterification zone 1 via recycle line 21. Line 20, which is removed from the overhead condenser, contains a very small fraction of the total material passing through line 19 and comprises light end materials produced in any of the aforementioned treatment or reaction zones which is removed from the process. Because of the nature of the operation in the evaporation zone, line 20 is generally connected to an ejector and a vacuum is drawn on the overhead condenser system 6 via line 20.

The other stream produced in the evaporation zone 5 is termed a high boiling bottoms product which is preferably removed from the process via line 18. Because of the nature of the material representing the high boiling bottoms product (high boiling organics, ash and in some instances esterification zone catalyst), it is desirable to remove at least a portion or preferably all of this material from the process through purge.

DETAILED DESCRIPTION OF THE INVENTION

The present invention is primarily concerned with the oxidation of a mother liquor stream which has been separated from a crystalline dimethyl ester product produced in an esterification zone and the subsequent treatment of a portion of the oxidized mother liquor stream in an evaporation treatment zone. In the evaporation treatment zone a low boiling overhead product containing diester precursors is recovered and returned to the esterification reaction zone. A high boiling bottoms product containing high boiling organics, ash and in some instances esterification reaction zone catalyst is also recovered from the evaporation zone which is removed in a preferred instance as a purge from the overall processing scheme.

The process into which the above described combination is incorporated has an overall flow scheme as described in the description of the drawing above. Therein the esterification zone can be operated at temperatures well known in the art in order to induce the esterification of the phenylene dicarboxylic acid (generally terephthalic or isophthalic acid) with a lower alkyl alcohol such as methanol thereby forming the dimethyl ester along with certain other by-product materials. The esterification zone typically uses very small quantities of catalyst, generally on the order of around 0.05% catalyst based on the feed to the esterification zone. Preferably the catalyst is a zinc oxide powder. The reaction temperatures, pressures and overall flow and reactor design for the esterification zone are relatively well known in the art and it is not considered necessary for one having ordinary skill in the art to elaborate on these particulars. The same holds for the cooling zone wherein the dimethyl esters are separated as a solid crystalline product from a mother liquor stream, since this operation is typically performed by using known filtration or centrifugation methods. It is not especially critical to the overall process or the improvement as claimed herein to select methods, operating temperatures and pressures and detailed description of the apparatus needed to perform this function.

Likewise, the flash zone which is utilized to remove the alcohol, water and some light esters from the mother liquor which has been separated from the dimethyl crystal product should generally be run at temperature, pressure and overall conditions and in an apparatus well known in the art for such purposes.

The oxidation reaction zone performs the essential function of oxidizing certain of the impurities remaining in the mother liquor before it is returned to the esterification zone or passed to the evaporation zone as will be described below. Specifically, reaction conditions within this zone should generally include temperatures known in the art and generally within the range of about 180° to about 250° C. or higher. More preferred temperature ranges should be within the range of from about 215° to about 225° C. with an especially preferred range being around 220° C. It is generally necessary, at least when operating at pressures of around one atmosphere and using air as the oxygen-containing medium, that temperatures greater than about 210° C. be maintained in order to achieve an over-rich vapor phase since the explosive range for equilibrium vapor concentrations is explosive within the range of from about 130° to about 202° C. at one atmosphere pressure.

The pressures within the oxidation reaction zone can vary within the well-known ranges. Primarily in order to reduce the cost of operating this particular apparatus and associated equipment, it is generally preferred to operate around atmospheric pressure but this is not a criticality.

The typical apparatus design for an oxidation reaction zone would generally be a reaction zone having the oxygen in upflow arrangement with baffling or impelling mixers present in such zone in order to adequately contact the mother liquor passed into the stream with the molecular oxygen passing through the zone.

The primary purpose for the use of the oxidation reaction zone is to convert certain impurities present in the mother liquor to dimethyl ester precursors through the mechanism of oxidation. In particular, the impurities generally treated in the oxidation reaction zone include, depending on the acid used in the esterification zone, the methyl esters of toluene and benzaldehyde. In instances in which terephthalic acid is used as the acid feed to the esterification zone, these impurities are described as p-methyltoluate and methyl-4-carboxybenzaldehyde. The other impurities, namely, the high boiling organics, ashes and in some instances esterification zone catalyst also are exposed to oxygen in the oxidation reaction zone and to some extent are converted to more oxidized components.

The reactions taking place in the oxidation reaction zone include the oxidation of the aforementioned methyl esters of carboxybenzaldehyde and toluic acid to their respective methyl ester acids. The methyl ester acids are generally termed diester precursors since when they are recycled to the esterification zone their acid moiety is esterified with alcohol thereby forming the diester product which can be recovered from the process.

Other precursors include the oxygenation product of bis (carbomethoxy) benzylbenzoate, specifically 4,4'-dicarboxybenzyl benzoate. This material boils within the high boiling organic boiling range and is produced in fairly large quantities when terephthalic acid feed is used in the esterification zone. Upon oxidation the bis (carbomethoxy) benzylbenzoate is thought to be converted to an anhydride at the bridge connecting its two aromatic moieties. After formation of the anhydride it is believed that it combines with water or methanol to form additional acids or esters giving increased product yields.

It is important to oxidize essentially all of the mother liquor to recover a maximum quantity of diester precursors since they appear in both the high boiling and low boiling fractions of the mother liquor. If a portion of the mother liquor is removed prior to oxidation then it is entirely possible that a reduction in diester yield will result.

The oxidation conditions effected in the oxidation reaction zone generally are performed without the use of a catalyst since applicants have found that suitable conversion of the methyl esters of benzaldehyde and toluene and the bis (carbomethoxy) benzylbenzoate can be effected when using only thermal oxidation. In some instances, however, oxidation may take place with or without molecular oxygen and with or without the presence of an oxidation catalyst or promoter. Of course, it is possible that in a system in which no external catalyst is added to the oxidation reaction zone, there may be inherent catalytic sites within the oxidation reaction zone by virtue of the material selected for its construction or the impurities which reside within such reaction zone or in the streams passing thereto.

The operating conditions which take place in the evaporation zone are generally regulated to effect the separation of the oxidized mother liquor fed to the evaporation zone into a high boiling bottoms product comprising high boiling organics, ash and in some instances esterification zone catalyst, and a low boiling overhead product which comprises in part the oxidized methyl esters of methyl-4-carboxybenzaldehyde and p-methyl toluate) together with some diester product and oxidized bis (carbomethoxy) benzylbenzoate. The low boiling overhead product can be returned to the esterification zone for conversion of the above described materials to diester product. The high boiling bottoms product is recovered as a bottoms product and removed from the process as a purge stream.

The purge effectively prevents a buildup in any or all of the processing units of solid materials and/or sludge caused by recycle of the high boiling organics, ash, and/or entrained esterification zone catalyst solids. This purge also essentially eliminates loss of product diester or any of its precursors since these materials are removed from the high boiling material by the evaporation treatment and returned to the esterification reactor.

One of the important advantages in utilizing the evaporation zone in conjunction with the oxidation zone is that the combination allows the removal of high boiling bottoms material from the evaporation zone while substantially minimizing the losses of diester product or diester precursors via the bottoms purge. If a purge is taken of straight mother liquor, whether or not oxidized, increased losses of diester product will result since it is present in the mother liquor. If the mother liquor is not oxidized then there is a further reduction in diester product yield since there is no production of methyl ester acid which can be converted to diesters.

Because of the nature of the high boiling bottoms stream which is desired to be contacted in the evaporation treatment zone, it is especially preferred in this zone that separation of the low boiling overhead product from the high boiling bottom product be effected by contacting the oxidized mother liquor feed with a hot surface thereby effecting evaporation of overhead product from a high boiling bottoms product which typically will remain on the hot surface. One of the methods of utilizing such a processing sequence is through incorporation of a wiped film evaporator. In such an apparatus, the oxidized mother liquor stream fed thereto contacts the hot walls of the evaporator causing the low boiling overhead portion to be evaporated. The remaining high boiling fraction in the form of a solid or semi-solid which remains on the hot walls is physically scraped or removed from the walls and recovered. Because the residual product is extremely high in viscosity, it is very much susceptible to forming heavy solids deposits on the walls of the hot surface it contacts, the use of a distillation columns as known in the art is generally not used.

The operating temperatures and pressures of the evaporation treatment zone can be selected from those fairly well known in the art and should include temperatures in the range of around 220° C. and pressures, preferably vacuums, generally in the range of from about 0.04 to about 0.05 kilograms per square centimeters absolute. In effecting the evaporation treatment of the portion of the oxidized mother liquor stream passed into the evaporation zone, an especially preferred operation will allow essentially 20 wt% of the oxidized mother liquor fed thereto to be removed from the evaporation zone as a high boiling bottoms product with about 76 wt% of the feed to the evaporation zone resulting in a low boiling overhead product which preferably is recycled to the esterification zone for the production of additional dimethyl esters. The remaining 4 wt% of the feed to the evaporation zone may be lost via the vacuum lines when inducing a vacuum into the overhead section of the evaporation zone. It is entirely possible, depending upon the operating conditions, catalyst used, specific feeds to the esterification zone and other operating variables affecting the production of the dimethyl ester to vary the ratio of low boiling overhead product to the high boiling bottoms product. It is especially preferred during steady state operations that the quantity of high boiling bottoms product removed from the process by regulated so as to minimize the loss of any valuable products which are present in this stream. If the evaporation zone is properly regulated with respect to operating temperatures and throughputs, the high boiling bottoms product removed from this stream will contain a minimum quantity of valuable dimethyl esters and dimethyl ester precursors.

The other important variables which can be regulated to the effect of the improvement claimed herein resides in the quantity of the mother liquor which is oxidized. It is preferred that essentially all of the mother liquor which is directly recycled to the esterification zone or indirectly recycled to the esterification zone (via the low boiling overhead product recycled from the evaporation zone) be oxidized. It is especially preferred that essentially all of the mother liquor removed from the dimethyl ester product be oxidized. Of course normal sampling and leakage will in most instances prevent oxidizing all the mother liquor.

Additionally, the ratio of the oxidized mother liquor which is fed directly to the esterification zone (via line 16 of the drawing) to that mother liquor which is indirectly recycled to the esterification zone (via lines 17, 19 and 21 of the drawing) can be regulated so as to effect the overall desired advantages described above. Specifically, when all or essentially all of the mother liquor is oxidized it is especially preferred that less than 98 wt% of such oxidized mother liquor be fed directly to the esterification zone with the remaining portion of the oxidized mother liquor passed directly to the evaporation zone. At steady state conditions it is also preferred that greater than 80% of the oxidized mother liquor be passed directly to the esterification zone with the remaining portion of the oxidized mother liquor being indirectly recycled by first being passed to the evaporation zone for the aforementioned evaporation treatment. Again, in instances when essentially all of the mother liquor stream is oxidized and essentially all of the oxidized mother liquor is returned to the esterification zone either directly or indirectly (through the evaporation zone) that from about 85-95 wt% of the oxidized mother liquor material is fed directly to the esterification zone with the remaining 15-5 wt% of the oxidized mother liquor stream passed directly to the evaporation zone. It is especially preferred that approximately 90 wt% of the oxidized mother liquor be passed directly to the esterification zone with the remaining 10 wt% of the mother liquor passed to the evaporation zone for separation into a low boiling overhead product and a high boiling bottoms product with essentially total recycle of the low boiling overhead product to the esterification zone.

The effluent stream from the esterification zone described above contains material termed high boiling organics. This material for purpose of definition includes organics in the broad sense which have boiling points above that of methyl trimellitate. In determining this component a distillation is performed at 194° C. and 12 mm Hg pressure with the material remaining as bottoms referred to as high boiling organics.

Typically the high boiling organics will contain materials referred to as ash. The ash component is essentially non-distillable and is determined by subjecting a sample to be analyzed for ash content to the following general procedures.

A sample of about 25-35 g. is placed in a platinum dish and ignited until the sample no longer supports visible combustion. Then the remaining sample is subjected to oxidation at 300° C. in air for about one hour. The remaining material (ash) is then calculated as a percentage of the original sample for ash content.

The high boiling bottoms product from the evaporation treatment zone will vary in composition depending primarily on the operating condition in that zone. It will contain a fairly high concentration of the above defined high boiling organics including ash. The separation of these materials from dimethyl esters and mono methyl esters results in the latter also being present in the high boiling bottoms product from the evaporation treatment zone. A typical high boiling bottoms product from the evaporation zone will contain about 20 wt.% of high boiling organics and esters boiling above monomethyl phthalate, about 44 wt.% monomethyl phthalate with the remaining 36 wt.% comprising dimethyl ester product.

The following examples are presented to illustrate specific embodiments of the improvement described herein and are not necessarily presented so as to unduly limit the scope of the claims.

EXAMPLE 1

In this example oxidation was performed in a round bottom flask fitted with a stirrer and a glass inlet tube. A glass wash bottle was used which contained a fritted glass bottom in order to allow a better contacting of air with the liquid being oxidized. For a typical oxidation run about 150 grams of a commercial mother liquor stripper bottoms material was placed in the glass wash bottle. The wash bottle was placed in an oil bath which was regulated by thermostat at either 200° or 220° C. The wash bottle was purged with nitrogen as it was heated to the given reaction temperature. When the reaction temperature was obtained, air was introduced into the reaction vessel at 393 milliliters per minute (one atmosphere) for an hour. After the hour of oxidation the contents in the reactor were poured out, allowed to solidify, then thoroughly ground and analyzed.

The data shown in the following tables illustrate the substantial reduction via oxidation of both methyl-4- carboxy-benzaldehyde and p-methyl toluate, each being converted to its respective mono methyl esters of terephthalic acid.

TABLE 1

| Sample Description | Initial wt. % methyl-4-carboxy-benzaldehyde | wt. % after 60 min. oxidation at 200° C. | wt. % after 60 min. oxidation at 220° C. |
|---|---|---|---|
| 1 | 3.9 | 1.59 | 0.0081 |
| 2 | 3.6 | 1.13 | 0.0093 |
| 3 | 3.1 | 0.013 | — |
| 4 | 3.5 | 0.017 | — |
| 5 | 4.3 | 0.034 | 0.0087 |
| 6 | 4.06 | 0.054 | — |
| 7 | 3.38 | 0.012 | — |
| 8 | 4.42 | — | 0.0086 |
| 9 | 3.91 | 0.014 | — |
| 10 | 3.68 | 0.021 | — |
| 11 | 2.96 | 0.012 | — |
| 12 | 3.65 | 0.007 | — |
| 13 | 3.57 | 0.960 | 0.67 |
| 14 | 4.53 | 0.004 | — |
| 15 | 4.60 | 0.004 | 0.011 |

TABLE 2

| Sample Description | Initial wt. % p-methyl toluate | wt. % after 60 min. oxidation at 200° C. | wt. % after 60 min. oxidation at 220° C. |
|---|---|---|---|
| 1 | 1.1 | 0.38 | — |
| 2 | 1.0 | 0.20 | — |
| 3 | 0.59 | 0.0009 | — |
| 4 | 0.60 | 0.012 | — |
| 5 | 0.85 | 0.033 | — |
| 6 | 0.81 | 0.034 | — |
| 7 | 0.52 | 0.001 | — |
| 8 | 0.66 | — | 0.0087 |
| 9 | 0.65 | 0.001 | — |
| 10 | 0.66 | 0.003 | — |
| 11 | 0.70 | — | — |
| 12 | 0.83 | 0.002 | — |
| 13 | 0.78 | 0.25 | 0.29 |
| 14 | 1.04 | — | — |
| 15 | 0.98 | — | — |

EXAMPLE 2

In this example, a mother liquor stripper bottoms stream from a commercial dimethylterephthalate production unit was oxidized using the procedure which is generally described for Example 1 except that the temperature was maintained at 200° C. during the oxidation step. The material which was oxidized together with the oxidized product were analyzed to determine the degree of conversion of the methyl-4-carboxybenzaldehyde and p-methyltoluate to mono methyl terephthalate. Additionally, high boiling organic content was measured to determine the extent of reduction of these materials together with the extent of their conversion to usable dimethylterephthalate precursors which if fed to the esterification zone would result in additionally gained product yields of diester.

The results of the product analysis are shown in Table 3 below and indicate that essentially all of the p-methyltoluate and methyl-4-carboxybenzaldehyde were converted to their respective mono methyl terephthate esters. Additionally, a substantial reduction in the quantity of high boilers material was realized by the oxidation procedure which results in an improved product yield since a portion of these high boiling materials were converted to diester precursors which when fed back to the esterification zone result in additional product diester.

TABLE 3

| Component | Analysis Initial | Final |
|---|---|---|
| P-methyl toluate, wt. % | 0.72 | 0.015 |
| methyl-4-carboxy benzaldehyde, wt. % | 3.08 | 0.062 |
| High boilers, ppm | 14,888 | 11,524 |

EXAMPLE 3

In this example a commercially produced mother liquor stripper bottoms stream was oxidized using conditions and procedures identical to those described for Examples 1 and 2 above. More particularly, a stream which contained approximately 63.88 wt.% of dimethylterephthalate, 22.7 wt.% of mono methyl terephthalate, 0.72 wt.% p-methyl toluate, 3.08 wt.% methyl-4-carboxybenzaldehyde, 2.04 wt.% terephthalic acid and approximately 14,888 ppm of high boiling organics was oxidized using the aforesaid procedures. After oxidation the mono methyl terephthalate concentration had increased 3.0 wt.%, the terephthalic acid content increased 0.3 wt.% with corresponding decreases of the p-methyltoluate and the methyl-4-carboxybenzaldehyde of 0.7 and 3.02 wt.%, respectively. Furthermore, there was a noticeable decrease in the concentration of the high boiling organics from the initial 14,888 ppm concentration to a post oxidation concentration of 11,524 ppm. Of important significance in the oxidation procedure was the reduction in the high boiling organics and in particular, the decrease in the concentration of bis (carbomethoxy)benzylbenzoate (specifically, 4,4'-dicarboxybenzyl benzoate) from an initial concentration of 6,140 ppm to a post-oxidation concentration of 107 ppm. The substantial decrease in this component is quite important for its oxidation product yields diester precursors such as mono methyl terephthalate or dimethyl terephthalate itself. The results of the oxidation of the mother liquor stream and in particular, the high boiling aspects of this stream, are shown for the high boiling organics only in Table 4 attached.

TABLE 4

| High Boiling Organics (Methyl Esters) | Concentration, ppm Initial | Post Oxidation |
|---|---|---|
| Dicarboxybiphenyl Isomers[A] | 712 | 811 |
| Dicarboxyindane | 12 | 7 |
| Bis (Carboxyphenyl) methane | 120 | 107 |
| 1,2,3,5-Tetracarboxybenzene | 33 | 33 |
| Unidentified[B] | 24 | 6 |
| Carboxybenzophenone | 45 | 39 |
| 4,4'-Dicarboxybiphenyl | 2,400 | 2,403 |
| Carboxybenzyl Toluate | 51 | 26 |
| Bis (4-carboxyphenyl) Methane | 16 | 17 |
| Cis 4-4'-Dicarboxystilbene | 62 | 4 |
| 4,4'-Dicarboxybenzophenone | 710 | 676 |
| 2,4',5-Tricarboxybiphenyl | 2,200 | 3,471 |
| Tricarboxy biphenyl[C] | 210 | 89 |
| Unidentified[B] | 180 | 142 |
| Tricarboxydiphenylmethane | 11 | 53 |
| 2,6-Dicarboxyfluorenone | 60 | 961 |
| 4,4'-Dicarboxybenzyl benzoate | 6,140 | 107 |
| Trans-4,4'-Dicarboxystilbene | 230 | 214 |
| Unidentified[B] | 1,672 | 2,358 |
| Total | 14,888 | 11,524 |

[A]includes all isomers not possible to specifically identify.
[B]structure not known.
[C]specific isomer not identified.

EXAMPLE 4

In this example samples 1, 2, 3, 4, 5 and 8 of Example 1 were analyzed for metals content. The metal content is reported in Table 5 below and represents the ppm concentration in the total mother liquor stripper bottoms stream from a commercial unit. The metals are present in the high boiling bottom material eventually removed from the evaporation zone in the process of this invention and are considered as part of the ash present therein.

Table 5

| Sample Description | Component content, ppm | | | | Total ppm |
|---|---|---|---|---|---|
| | Br | Co | Fe | Mn | |
| 1 | 574 | 312 | 77 | 1592 | 2555 |
| 2 | 497 | 250 | 64 | 1388 | 2199 |
| 3 | 368 | 220 | 67 | 1049 | 1706 |
| 4 | 321 | 229 | 112 | 1370 | 2032 |
| 5 | 593 | 258 | 98 | 1554 | 2513 |
| 6 | 568 | 203 | 105 | 1125 | 2001 |

EXAMPLE 5

In this example a mother liquor stripper bottoms stream from a commercial dimethyl terephthalate production unit was treated in an evaporation zone to illustrate the separation of low boiling overhead material from a high boiling bottoms material which contained high boiling organics.

The evaporation treatment zone in this example was a wiped film evaporator having about 0.125 square meters surface area. The evaporator had an 82 mm inside diameter with a single heating section about 500 mm long. The rotor in the evaporator had four blades and during the run was maintained at a constant 2,000 RPM during operation. The blades of the rotor were designed to have a close tolerance to the walls of the evaporator to scrape the high boiling bottoms from the wall for eventual recovery.

The mother liquor stripper bottoms was fed to an agitated jacketed feed holding tank where it was maintained in a liquid state. The resulting melt was fed via a suitable pumping means to the wiped film evaporator. A high boiling bottoms material from the evaporator was collected in a bottom collection drum while the low boiling overhead material was passed through a down flow glycol cooled heat exchanger where condensation occurred. The distillate thus obtained was collected in a recovery drum while uncondensed vapors were passed through a hot water cooled cold trap and from there to a series of jets which generated a vacuum on the system. Periodic sampling of the overhead and bottoms streams was performed to determine the separation effected by the evaporation treatment zone.

A run of collected bottoms from previous runs was also processed. In this case the feed to the evaporation zone was a high boiling bottoms product.

Runs 1-3 in Table 6 below were on mother liquor stripper bottoms material while run 4 used a bottoms product as feed illustrating the effects of reconstituting a high boiling bottoms material.

Table 6

| Parameters | Run No. | | | |
|---|---|---|---|---|
| | 1 | 2 | 3 | 4 |
| Feed rate, Kg/hr. | 34.8 | 23.4 | 28.8 | 16.2 |
| Distillate rate, Kg/hr. | 22.2 | 17.5 | 25.4 | 4.2 |
| Bottoms rate, Kg/hr. | 13.4 | 5.22 | 3.24 | 5.9 |
| Heating medium temperature, ° C. | 255 | 259 | 265 | 265 |
| Cooling medium temperature, ° C. | 145 | 145 | 145 | 145 |
| Vapor temperature, ° C. | 196 | 190 | 186 | 199 |
| Bottoms temperature, ° C. | 203 | 200 | 200 | 204 |
| Pressure at exit, mm Hg. obs. | 58[(1)] | 35 | 30 | 25 |
| Bottoms/Feed × 100, % | 38.5 | 22.3 | 11.3 | 36.4 |

The bottoms streams produced for runs 1, 2, 3 and 4 above were analyzed for metals content by x-ray fluorescence and for ash content and are reported in Table 7 below.

Table 7

| Steam Description | Component Description | | | | | |
|---|---|---|---|---|---|---|
| | Ash | Bromine | Cobalt | Iron | Manganese | Zinc |
| Run 1 Overhead, ppm | 40 | 74 | 3 | — | 3 | 3 |
| Bottoms, ppm | 14,900 | 510 | 250 | — | 920 | 14,000 |
| Run 2 Overhead, ppm | 11 | 79 | 3 | — | 3 | 3 |
| Bottoms, ppm | 22,400 | 700 | 380 | — | 1,400 | 1,400 |
| Run 3 Overhead, ppm | 19 | 90 | 3 | — | 3 | 3 |
| Bottoms, ppm | 37,700 | 800 | 520 | — | 2,200 | 2,300 |
| Run 4 Overhead, ppm | 24 | 109 | 3 | 6 | 3 | 3 |
| Bottoms, ppm | 62,900 | 3,600 | 1,500 | 2,100 | 5,300 | 41,000 |

EXAMPLE 6

In this example there is illustrated the overall claimed process including the oxidation of essentially all the mother liquor stripper bottoms together with evaporation treatment of a slip stream from the oxidation zone. In order to simplify the illustration certain operations such as heat exchange, pressure, level and flow control have been omitted.

The oxidation zone is maintained at about 220° C. and a pressure of about 1.49 Kg/cm$^2$ absolute. Air is fed up-flow to the oxidation zone which performs its function in the absence of added oxidation catalyst.

The wiped film evaporation zone is maintained at around 220° C. on the film side of the unit. The feed to this unit is at about 200° C. and 1.010 Kg/cm$^2$ absolute pressure. Essentially all of the high boiling bottoms from the evaporation zone is purged from the system.

Tables 8, 9 and 10 below show the concentrations and conditions of relevant components and processing streams with reference to the drawing described above.

The light esters listed in the tables generally comprise methylbenzoate while the other esters generally comprise esters boiling above monomethyl terephthalate. The high boiling organics as used in the claims and specifications generally include the last two listed components in such tables.

Table 8

| | Steam Description | | |
|---|---|---|---|
| | 12 | 13 | 14 |
| Component, Kh/hr. | | | |
| Air. | — | 28.10 | 31.00 |
| Methanol | 2.80 | 0.91 | — |
| Water | 3.10 | 13.20 | — |
| Light Esters | 13.30 | — | — |
| P-methyl toluate | 3.90 | — | — |
| methyl-4-carboxybenzaldehyde | 16.80 | — | — |
| Dimethyl terephthalate | 1477.70 | — | — |
| Dimethyl iso or ortho | | | |

Table 8-continued

| | Steam Description | | |
|---|---|---|---|
| | 12 | 13 | 14 |
| phthalate | 74.10 | — | — |
| Mono methyl terephthalate | 392.70 | — | — |
| Heavy esters | 34.00 | — | — |
| High boiling components and ash | 70.00 | — | — |
| Total | 2088.40 | 42.20 | 31.00 |
| Pressure, Kg/cm²/abs. | — | 1.03 | 1.49 |
| Temperature, °C. | 220 | 74 | 220 |

Table 9

| | Steam Description | | |
|---|---|---|---|
| | 16 | 17 | 18 |
| Component, Kh/hr. | | | |
| Air | — | — | — |
| Methanol | — | — | — |
| Water | — | — | — |
| Light Esters | 9.00 | 1.00 | — |
| P-methyl toluate | — | — | — |
| Methyl-4-Carboxybenzaldehyde | 16.80 | — | — |
| Dimethyl terephthalate | 1291.60 | 143.40 | 13.50 |
| Dimethyl iso or ortho phthalate | 64.60 | 7.20 | 0.70 |
| Mono methyl terephthalate | 370.60 | 41.20 | 17.60 |
| Heavy esters | 30.60 | 3.40 | 2.00 |
| High boiling components and ash | 63.00 | 7.00 | 6.70 |
| Total | 1829.4 | 203.20 | 40.50 |
| Pressure, Kg/cm²/abs. | — | — | — |
| Temperature, °C. | 220 | 220 | 200 |

Table 10

| | Steam Description | | |
|---|---|---|---|
| | 20 | 21 | 22 |
| Component, Kg./hr. | | | |
| Air | 1.00 | — | — |
| Methanol | — | — | — |
| Water | — | — | 156.90 |
| Light Esters | 0.40 | — | 3.30 |
| P-methyl toluate | — | — | — |
| methyl-4-carboxybenzaldehyde | — | — | — |
| Dimethyl terephthalate | 6.50 | 123.40 | 42.70 |
| Dimethyl iso or ortho phthalate | 0.30 | 6.20 | 2.30 |
| Mono methyl terephthala | 0.20 | 23.40 | 4.00 |
| Heavy esters | — | 1.40 | — |
| High boiling components and ash | — | 0.30 | — |
| Total | 8.40 | 155.30 | 209.20 |
| Pressure, Kg/cm² abs. | 0.04 | 0.04 | — |
| Temperature, °C. | 154 | 154 | 74 |

We claim as our invention:

1. In a process for the production of a lower alkyl diester of a phenylene dicarboxylic acid in an esterification zone wherein reaction product from said zone is cooled thus rendering a mass of lower alkyl diester and mother liquor containing impurities characterized as high boiling organics and methyl esters of carboxybenzaldehyde and toluic acid, wherein an improvement comprises:
   1. Oxidation treatment of mother liquor with molecular oxygen at a temperature in the range of from about 180° to about 250° C. to form a product termed oxidized mother liquor and return of part of said oxidized mother liquor to the esterification zone;
   2. Evaporation treatment of another part of said oxidized mother liquor to effect production of low boiling overhead product and high boiling bottoms product containing said high boiling organics;
   3. Return of overhead product to the esterification zone and removal of high boiling bottoms product from the process.

2. The process of claim 1 wherein said dicarboxylic acid is terephthalic acid.

3. The process of claim 1 wherein said oxidation treatment includes contacting said mother liquor with air.

4. The process of claim 3 wherein said oxidation treatment is performed as essentially thermal oxidation.

5. The process of claim 1 wherein less than about 98 weight percent of the oxidized mother liquor is passed directly to the esterification zone and the remaining oxidized mother liquor is passed to said evaporation treatment.

6. The process of claim 1 wherein the oxidation treatment comprises conversion of methyl esters of carboxybenzaldehyde and toluic acid to methyl esters of phenylene carboxylic acid.

7. The process of claim 1 wherein essentially all the mother liquor is subjected to oxidation treatment.

8. The process of claim 1 wherein said evaporation treatment comprises contacting oxidized mother liquor with a hot surface thereby causing overhead product to be vaporized and removing from the surface the high boiling bottoms product.

9. The process of claim 8 wherein the evaporation treatment is effected in a wiped film evaporator.

10. The process of claim 1 wherein essentially all the mother liquor is subjected to oxidation treatment and from about 85 to about 95 weight percent of said oxidized mother liquor is passed as recycle directly to said esterification zone, with the remaining oxidized mother liquor passed to said evaporation treatment.

11. The process of claim 10 wherein the dicarboxylic acid is terephthalic acid.

12. The process of claim 10 wherein said oxidation treatment is effected by contacting mother liquor with air.

13. In a process for the production of methyl esters from phenylene dicarboxylic acid and methyl alcohol in an esterification zone wherein reaction product from said zone is cooled thus rendering a mass of dimethyl ester crystals separable from remaining mother liquor containing impurities characterized as high boiling organics (including bis( carbomethoxy) benzylbenzoate) and methyl esters of carboxybenzaldehyde and toluic acid, wherein mother liquor is stripped of light ends including water and unreacted alcohol in a stripping zone yielding a mother liquor stripper bottoms, wherein an improvement comprises:
   1. Oxidation of substantially all the mother liquor stripper bottoms in an oxidation zone at oxidizing conditions including the presence of molecular oxygen to effect the conversion of the methyl esters of carboxybenzaldehyde and toluic acid to the mono methyl esters of phenylene dicarboxylic acid producing an oxidation zone effluent termed oxidized mother liquor stripper bottoms;
   2. Passing at least 75 weight percent of said oxidized mother liquor stripper bottoms as recycle directly to the esterification zone;
   3. Passing the remaining oxidized mother liquor stripper bottoms to an evaporation zone to effect production of low boiling overhead product including said mono methyl esters of phenylene dicarboxylic acid and high boiling bottoms product including said high boiling organics;
   4. Return of substantially all said overhead product to said esterification zone; and 5. Recovery and purging from the process high boiling bottoms product.

14. The process of claim 13 wherein said dicarboxylic acid is terephthalic acid.

15. The process of claim 13 wherein said oxygen is present in air.

16. The process of claim 13 wherein said oxidation conditions include temperatures within the range of from about 190° C. to about 250° C.

17. The process of claim 16 wherein said temperatures are within the range of from about 210° C. to about 230° C.

18. The process of claim 13 wherein at least 85 weight percent of said oxidized mother liquor stripper bottoms is passed to said esterification zone with the remaining oxidized mother liquor stripper bottoms passed to said evaporation zone.

19. The process of claim 18 wherein about 90 weight percent of said oxidized mother liquor stripper bottoms is passed to said esterification zone with the remaining oxidized mother liquor stripper bottoms passed to said evaporation zone.

20. The process of claim 18 wherein the high boiling bottoms product from said evaporation zone comprises from about a few up to about 40 weight percent of the oxidized mother liquor stripper bottoms fed to said evaporation zone.

21. The process of claim 20 wherein the high boiling bottoms product from said evaporation zone comprises from about a few up to about 30 weight percent of the oxidized mother liquor stripper bottoms fed to the evaporation zone.

22. The process of claim 13 in that said evaporation zone effects the production of overhead and bottoms product by contacting oxidized mother liquor with a hot surface thereby causing overhead product to be vaporized and removing from the surface the bottoms product.

23. The process of claim 22 in that the evaporation treatment is effected by a wiped film evaporator.

* * * * *